(12) United States Patent
Hwang et al.

(10) Patent No.: US 9,012,685 B2
(45) Date of Patent: Apr. 21, 2015

(54) RECOVERY METHOD OF HIGHLY PURE LACTIC ACID AND ALKYL LACTATE

(75) Inventors: Dong Won Hwang, Anyang-si (KR); Jong-San Chang, Daejeon (KR); Young Kyu Hwang, Daejeon (KR); U-Hwang Lee, Daejeon (KR); HyoJin Gwak, Incheon (KR)

(73) Assignee: Korea Research Institute of Chemical Technology, Taejeon-si (KR)

( * ) Notice: Subject to any disclaimer, the term of this patent is extended or adjusted under 35 U.S.C. 154(b) by 671 days.

(21) Appl. No.: 13/310,050

(22) Filed: Dec. 2, 2011

(65) Prior Publication Data
US 2012/0142945 A1   Jun. 7, 2012

(30) Foreign Application Priority Data

Dec. 2, 2010   (KR) .................. 10-2010-0121960

(51) Int. Cl.
C07C 67/08      (2006.01)
C07C 51/493     (2006.01)
C12P 7/56       (2006.01)

(52) U.S. Cl.
CPC ............... *C07C 67/08* (2013.01); *C07C 51/493* (2013.01); *C12P 7/56* (2013.01)

(58) Field of Classification Search
CPC .............................. C07C 51/493; C07C 67/08
USPC ............................ 549/274; 435/135; 562/589
See application file for complete search history.

(56) References Cited

U.S. PATENT DOCUMENTS 5,210,296 A * 5/1993 Cockrem et al. ............... 562/589
6,280,985 B1 * 8/2001 Caboche et al. ............... 435/139

FOREIGN PATENT DOCUMENTS

| JP | 1995-194387 | A |   | 8/1995 |            |
|----|-------------|---|---|--------|------------|
| KR | 0698817     | B1 |  | 8/2005 |            |
| KR | 0762773     | B1 |  | 8/2005 |            |
| WO | WO03/014106 |   | * | 2/2003 | C07D 333/16 |
| WO | WO2009/062224 | | * | 5/2009 | C07D 319/12 |

OTHER PUBLICATIONS

Translation of WO2009/062224, May 22, 2009, pp. 1-31.*

* cited by examiner

*Primary Examiner* — Paul A Zucker
*Assistant Examiner* — Mark Luderer
(74) *Attorney, Agent, or Firm* — Lucas & Mercanti, LLP

(57) ABSTRACT

A method for recovery of highly pure alkyl lactate and lactic acid is provided, which includes a step 1 for producing source liquid comprising lactic acid or ammonium lactate; a step 2 for dehydrating the source liquid product of step 1; a step 3 for producing liquid mixture by sequentially adding and stirring alcohol and acid solution to the dehydrated source liquid; a step 4 for separating and removing ammonium salt precipitation from the liquid mixture of step 3; a step 5 for producing alkyl lactate from ammonium salt-free liquid mixture by esterification reaction; and a step 6 for separating alcohol and alkyl lactate by distillation from the mixture of step 5.

19 Claims, 3 Drawing Sheets

RECOVERY METHOD OF HIGHLY PURE LACTIC ACID AND ALKYL LACTATE

CROSS-REFERENCES TO RELATED APPLICATION

This patent application claims the benefit of priority from Korean Patent Application No. 10-2010-0121960, filed on Dec. 2, 2010, the contents of which are incorporated herein by reference.

BACKGROUND OF THE INVENTION

1. Field of the Invention

The present invention relates to a recovery method of highly pure alkyl lactate and lactic acid.

2. Description of the Related Art

There has been an increased amount of usage in lactic acid in recent years, which is a base material for biodegradable polymer, polylactic acid. Lactic acid is also widely used as the base material for chemistry, cosmetics and food. Lactic acid is generally produced by fermentation because production by fermentation is more environmentally friendly and economical than production by chemical synthesis.

Also, there has been an increasing demand for ethyl lactate, which can be used as food additives, spices, as well as an environmentally friendly solvent that can substitute the toxic halogen solvents because they are less volatile, have less odor, stable at temperatures over 150° C., have high solvency and are biodegradable. In addition, lactic acid can be used as a base material for lactide, which is the monomer of polylactic acid (PLA) that is becoming popular as a biodegradable polymer.

When producing lactic acid by fermentation, lactic acid is generally produced by fermentation process of carbohydrate such as glucose with anaerobic bacteria. To increase the fermentation productivity, lactic acid fermentation process is usually performed at pH range of 5 to 6. Basic compounds such as ammonia or calcium carbonate are added as pH regulators. Therefore, the lactic acid formed by above method will exist in the form of ammonium lactate or calcium lactate. Since the solubility of calcium lactate in water is less than 80 g/liter, the calcium lactate precipitate in the fermentation solution will inhibit the fermentation, limiting the final concentration of lactic acid to below 10%. Therefore, it is advantageous to use ammonium lactate form in the fermentation process in terms of productivity, since the fermentation concentration can be increased up to 20% due to its higher solubility in water.

Although the fermentation productivity of calcium lactate is very low, the lactic acid can be separated easily from the fermentation broth of calcium lactate by treating it with sulfuric acid followed by separation of calcium sulfate precipitate.

Therefore, calcium lactate fermentation method has been widely used for commercial lactic acid fermentation and purification process, despite the problem of calcium sulfate waste overproduction, known as gypsum.

Although the fermentation productivity of ammonium lactate is very high, its recovery process into lactic acid is quite complicated.

For example, U.S. Pat. No. 6,291,708 discloses a method for decomposing ammonium lactate liquid solution using high pressure, and U.S. Pat. No. 5,723,639 discloses a method for manufacturing lactic acid using electrodialysis method and membrane techniques. However, there are several problems; the high investment cost for equipments for dissociating at high pressure and membrane, the slow reaction rate, and finally, the low final concentration of lactic acid produced.

In addition, Korean Patent Application Laid-open Publication No. 2003-0030575 discloses a Method for increasing the production of lactic acid from food waste using enzyme hydrolysis and fermentation method, Korean Patent Application Laid-open Publication No. 2003-0008187 discloses a fermentation process using the fermentation medium containing lignocelluloses as the carbon source and inoculating the media with lactic acid-fermenting microorganism, Korean Patent Application Laid-open Publication No. 2003-0032982 discloses a method for producing lactic acid using natural culture media consisting of liquified/saccharified wheat bran without adding any other chemical materials, Korean Patent Application Laid-open Publication No. 10-2005-0097719 disclosed a method for producing lactic acid by producing saccharified solution from fibrous biomass at optimal temperature of the saccharification enzymes, and then adding the lactic acid-forming microorganism into the fermentor filled with the saccharified liquid, Korean Patent Application Laid-open Publication No. 10-2005-0010986 disclosed a method of producing lactic acid by using tapioca starch saccharified solution as the source material and culturing the lactic acid-fermenting microorganism for lactic acid biosynthesis, Korean Patent Application Laid-open Publication No. 10-2008-0065610 disclosed a microorganism with lactic acid-fermenting activity with part or all of its protein with 4-hydroxybenzoic acid polyprenyl transferase activity, or 2-octaprenylphenol 2-octapreny-6-methoxyphenol; flavin reductase activity are reduced or lost, in particular, a microorganism with all or part of its chromosomal DNA coding for proteins with 4-hydroxybenzoic acid polyprenyl transferase activity, or 2-octaprenylphenol 2-octapreny-6-methoxyphenol; flavin reductase activity is missing, and the method of producing lactic acid using the microorganism thereof.

However, the traditional techniques for producing lactic acid by fermentation fail to describe a recovery method of highly pure lactic acid.

In addition, lactic acid is produced by esterification reaction of ammonium lactate fermentation liquid with alcohol to form alkyl lactate, and then hydrolyzed to lactic acid. The esterification reaction between ammonium lactate and alcohol has low efficiency because of the catalyst inhibition by ammonium ion. Therefore, a high temperature/pressure condition is required to improve the efficiency, which may cause high costs. The production of lactic acid oligomer and lactamide as the reaction by-product may also cause a problem.

In addition, there is a method of treating ammonium lactate with sulfuric acid to convert into ammonium sulfate and lactic acid, but the solubility of ammonium sulfate is 74.4 g in 100 ml of water at 20° C., which is very high, therefore it is impossible to recover lactic acid from ammonium lactate using ammonium sulfate precipitation and filtration method.

In addition to the above recovery methods, there are other methods such as ion exchange, affinity, extraction and distillation for recovering lactic acid. Lactic acid has a very high affinity to water and alcohol, and is a nonvolatile (or very low volatile) material; so it is difficult to isolate it using distillation method which is widely used in the industry. Distillation under reduced pressure may be used, but a high vacuum pressure is required, which causes a problem of investment in extra plant and equipments.

Therefore, a technology for recovering lactic acid from the fermentation broth of ammonium lactate that is economical and gives higher yield than the conventional method is required.

Also, the lactic acid ester, alkyl lactate is a biodegradable ethyl lactate which is gaining importance for its wide usage as an environmentally friendly solvent. Similar with lactic acid, there is a high demand for economical techniques of recovering and purifying highly pure alkyl lactate from lactic acid fermentation liquid.

Therefore, the present inventors completed a recovery method of highly pure alkyl lactate by adding alcohol and sulfuric acid to the source liquid comprising lactic acid and ammonium sulfate that is cost effective than the conventional method; and also completed a recovery method of highly pure lactic acid by hydrolyzing pure alkyl lactate, which is cost effective than the conventional method.

DETAILED DESCRIPTION OF THIS INVENTION

Summary of the Invention

One object of the present invention is to provide a recovery method of highly pure alkyl lactate and lactic acid.

In order to achieve the objects, the present invention provides a recovery method of highly pure alkyl lactate which comprises a step for producing source liquid comprising lactic acid or ammonium lactate (step 1); a step for dehydrating the source liquid mixture product of step 1 (step 2); a step for producing liquid mixture by sequentially adding and stirring alcohol and acid solution to the dehydrated source liquid (step 3); a step for isolating and removing ammonium salt precipitation from the liquid mixture of step 3 (step 4); a step for producing alkyl lactate from the ammonium salt-free liquid mixture by esterification reaction (step 5); and a step for separating alcohol and alkyl lactate from the mixture product of step 5 by distillation (step 6), and a recovery method of highly pure lactic acid by recovering the hydrolyzed product of highly pure alkyl lactate recovered by the recovery method.

The recovery method of highly pure alkyl lactate and lactic acid of the present invention does not require the previous expensive pretreatment equipments such as electrodialys is apparatus or membranes. The recovery method has an effect of recovering highly pure lactic acid more economically than the traditional methods since alkyl lactate and lactic acid are produced at lower temperatures without any other catalysts added. And also, the recovery method can effectively separate and recycle the by-product, ammonium sulfate.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Hereinafter, the present invention will be described in more detail.

The present invention provides a recovery method of highly pure alkyl lactate which comprises a step for producing source liquid comprising lactic acid or ammonium lactate (step 1); a step for dehydrating the source liquid mixture product of step 1 (step 2); a step for producing liquid mixture by sequentially adding and stirring alcohol and acid solution to the dehydrated source liquid (step 3); a step for isolating and removing ammonium salt precipitation from the liquid mixture of step 3 (step 4); a step for producing alkyl lactate from the ammonium salt-free liquid mixture by esterification reaction (step 5); and a step for separating alcohol and alkyl lactate from the mixture product of step 5 by distillation (step 6).

Hereinafter, the present invention will be described in more detail.

The step 1 according to the present invention is a step for producing source liquid comprising lactic acid or ammonium lactate.

Preferably, the source liquid of step 1 is produced from lactic acid fermentation liquid. Lactic acid is a material widely used in food, chemical and pharmaceutical industries that are generally produced by synthesis. In general, fermentation is used as the production method for lactic acid due to its environmentally friendly and economic advantages. Therefore, in the present invention, lactic acid fermentation liquid was produced from step 1, and source liquid containing lactic acid or ammonium lactate was produced from the lactic acid fermentation liquid. Further, L-lactic acid, D-lactic acid and a racemic mixture of lactic acid may be used as source liquid, but is not limited thereto.

However, the lactic acid fermentation liquid may be fermented preferably by lactic acid-fermenting microorganism.

The lactic acid fermentation liquid may be produced by adding microorganism to the fermentation liquid containing plant source such as corn starch, sugar and cellulose, possible saccharification substrates such as algae and organic waste. More preferably, the lactic acid-fermenting microorganism may be *Lactobacillus paracasei*, but is not limited thereto.

Generally, acidic fermentation process has a disadvantage of low fermentation productivity when compared to neutral fermentation process. Preferably, the production of lactic acid fermentation is performed at ammonia containing neutral pH condition, therefore ammonia gas or ammonia solution may be added to produce the fermentation liquid containing ammonium lactate or ammonium lactate/lactic acid. Generally, the lactic acid fermentation liquid may be comprised of 20 weight % or lesser amount of ammonium lactate or ammonium/lactic acid as represented by Chemistry FIG. 1 or Chemistry FIG. 2.

Figure 1:
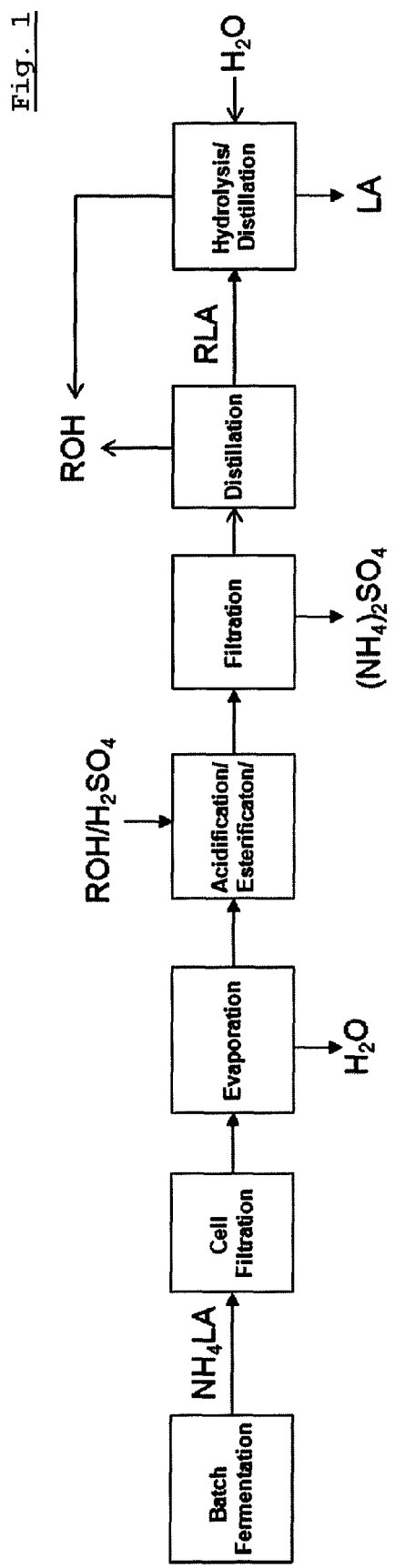
FIG. 1 is a flow diagram showing the process of the recovery method.

[Chemistry Figure 1]

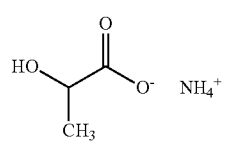

Figure 2:
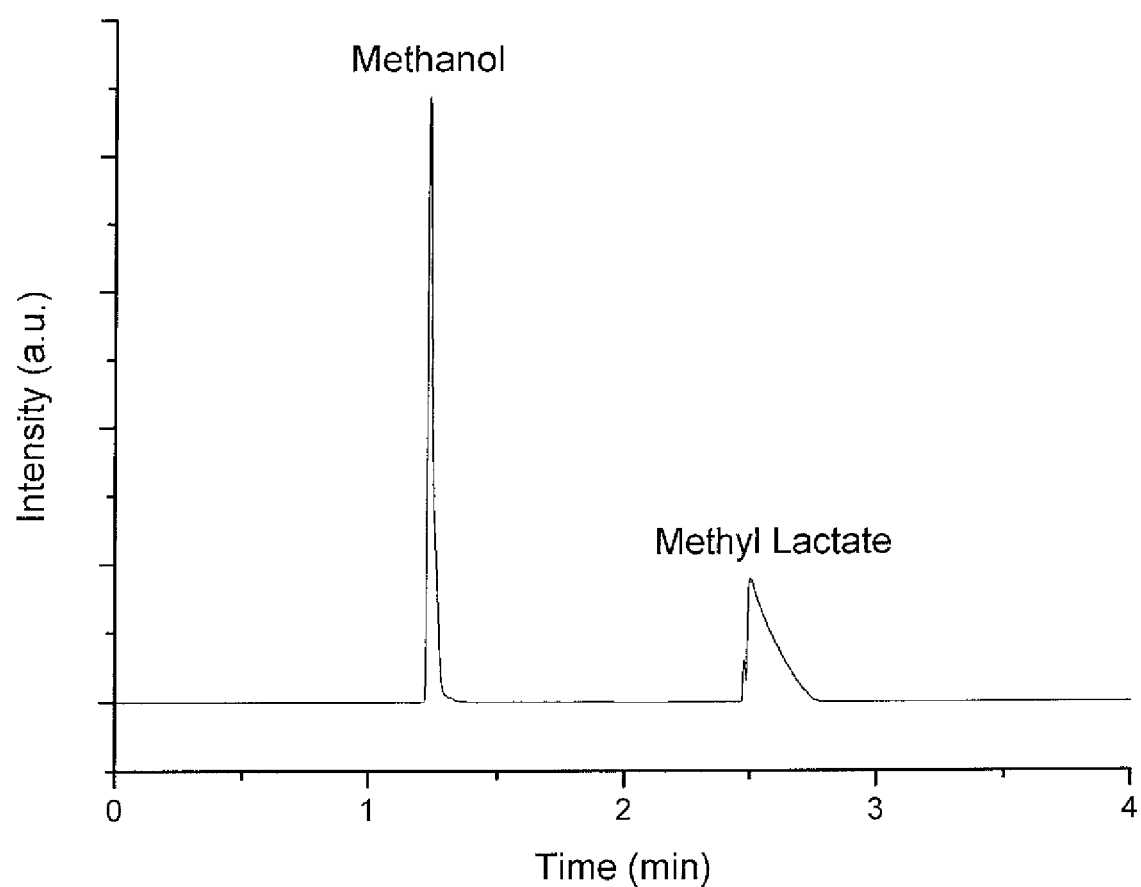
FIG. 2 is a graph showing the gas chromatography analysis of alkyl lactate produced from Example 1.

[Chemistry Figure 2]

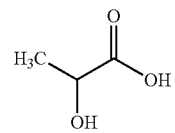

The step 2 is a step for dehydrating the source liquid of step 1.

The source liquid produced from step 1 contains excessive amount of water. Therefore, in step 2 of the present invention, excessive water in the source liquid is removed. Preferably, 50 to 95 weight % of water may be removed from the source liquid.

If more than 95 weight % of water is removed from the source liquid, a problem of lowered dehydration efficiency and lactic acid polymer formation may occur. When the water is removed lesser than 50 weight %, the high concentration of water may lead to decrease in the precipitation yield of ammonium sulfate in the following steps and also reduce the reaction rate of alkyl lactate synthesis.

Preferably, the hydration in step 2 may be performed at temperatures of 30-120° C.

When the dehydration in step 2 is performed at temperatures lower than 30° C., there is a problem of the dehydration speed decreasing, and if performed at temperatures over 120° C., lactic acid polymer may form.

Moreover, dehydration from step 2 is preferably performed under reduced pressure condition, but is not limited thereto.

The step 3 is sequentially adding and stirring alcohol and acid solution to the dehydrated source liquid from step 2.

The conventional technique described the method of converting ammonium lactate solution into ammonium sulfate and lactic acid by adding sulfuric acid to the solution. In this case, it is impossible to form precipitate at room temperature because solubility of ammonium sulfate in water is high. Therefore, a problem of having an additional treatment process such as chromatography method exists.

The alcohol solubility of ammonium salt produced by adding alcohol and acid solution in step 3 after fully removing water from the source liquid of step 2 is greatly reduced, which makes it easier for the precipitation to form without any extra treatment process.

The reaction of step 3 is represented by the Reaction Formula 1.

[Reaction Formula 1]
Reaction of lactic acid and ammonium sulfate formation

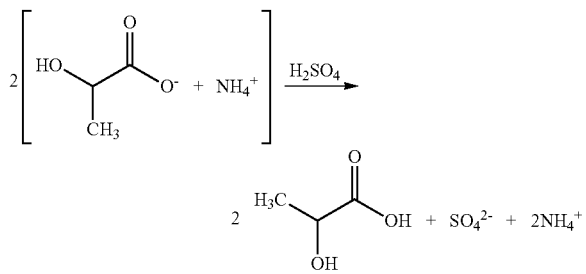

The alcohol added in step 3 is preferably selected from the group consisting of methanol, ethanol, normal propanol and isopropyl alcohol. The amount of alcohol added is preferably 1 to 10-foldmolar ratio of ammonium lactate or lactic acid contained in the source liquid, and more preferably, 2 to 5-fold molar ratio.

If the alcohol is added more than 10-fold higher molar ratio of ammonium lactate or lactic acid, the excessive amount of alcohol will cause an increase in the alcohol recovery cost in the following steps, and if alcohol is added lesser than 1-fold molar ratio, there is no increased effect by adding alcohol on ammonium sulfate precipitation.

However, the amount of acid solution added in step 3 is preferably 0.3 to 3-fold molar ratios to ammonium lactate or lactic acid in the source liquid, and more preferably 0.5 to 1-fold molar ratios.

If the acid solution in step 3 is added lesser than 0.3-fold molar ratio to ammonium lactate or lactic acid, the ammonium lactate does not fully convert to lactic acid, if added more than 3-fold molar ratio, the excessive amount of acid solution may cause a problem of erosion and increase in wear and tear expenses.

The acid solution in step 3 is preferably one selected from the group consisting of sulfuric acid, hydrogen iodide (HI), hydrogen bromide (HBr), nitric acid (HNO$_3$), hydrochloric acid (HCl), phosphoric acid (H$_3$PO$_4$) and perchloric acid (HClO$_4$) or mixed inorganic acid, more preferably sulfuric acid, which has low water concentration and is easy to handle.

The step 4 is a step of isolating and removing ammonium sulfate precipitation produced from step 3.

The method for isolating and removing ammonium sulfate precipitation in step 4 may be the conventional isolation and removing method, preferably the method is filtration.

The step 5 is a step for producing alkyl lactate by heating and esterification reaction using liquid mixture removed of ammonium salt precipitation.

The reaction of step 5 is represented by the Reaction Formula 2.

[Reaction Formula 2]
Reaction of alkyl lactate formation

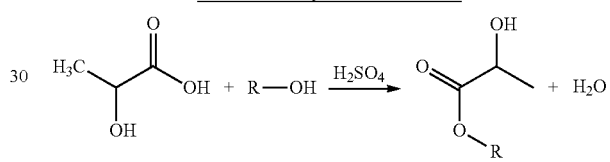

In step 3, during the process of converting ammonium lactate into lactic acid, alkyl lactate may be formed by part of the lactic acid while using remaining acid solution as catalyst. However, to increase the reaction rate, the temperature for the esterification reaction in step 5 is preferably at temperatures of 30 to 150° C. more preferably, at temperatures of 50 to 100° C.

If the esterification reaction is performed at temperatures below 30° C., a problem of slower reaction rate may occur, if the esterification reaction is performed at temperatures above 150° C., side reactions such as forming of lactic acid oligomer and increase in alcohol vaporization may happen, which may lead to an increase of energy waste expenses.

The step 6 is a step for separating alcohol and alkyl lactate from the mixture product of step 5 by distillation. The alcohol removed from this step is preferably recycled in step 2, and the recovered alkyl lactate may be used as it is or hydrolyzed to produce highly pure lactic acid. The separation of alcohol and alkyl lactate from the fermentation liquid may use the general reaction distillation method described previously.

Further, the esterification reaction from step 5 and distillation from step 6 may be performed simultaneously by reaction distillation, therefore alcohol and alkyl lactate may be separated from a single step.

The present invention provides a recovery method for highly pure lactic acid, wherein the lactic acid is produced by hydrolysis of highly pure alkyl lactate recovered by the recovery method.

The recovery method of highly pure lactic acid is a method for recovering lactic acid by hydrolyzing alkyl lactate, and may be performed in conjunction with the recovery method of alkyl lactate.

Preferably, the hydrolysis is performed at temperatures of 30 to 200° C., and more preferably at temperatures of 60 to 150° C.

If the hydrolysis reaction is performed at temperatures below 30° C., a problem of slower reaction rate may occur, and if the hydrolysis reaction is performed at temperatures above 200° C., problems such as induction of side reactions and energy loss may occur.

Preferably, the hydrolysis may be performed in hydrolysis reactor containing acid catalyst or base catalyst.

Acid catalyst has an effect on increasing hydrolysis of the recovery method. Acid catalyst is selected from the group consisting of sulfuric acid, Amberlyst, Nafion, Nafion-silica composite, Keggin type hetero-poly acid, $Hb_2O_5$, $HNbMoO_6$, zeolite and $H_{(8-n)}XM_{12}O_{40}(X=Si^{4+}, P^{5+}/M=W^{6+}, Mo^{6+})$, more preferably the acid catalyst is Amberlyst, which is easy to recover and has high acidity.

Moreover, the base catalyst has an effect on increasing hydrolysis of the recovery method. Base catalyst is preferably selected from the group consisting of alkali or alkali earth metal hydroxide, basic hydroxide containing alkali or alkali earth metal ion, and hydrotalcite-class Layered Double Hydroxide (LHD), more preferably the base catalysts are basic oxide and LDH, which are easy to recover and have high basicity.

The highly pure alkyl lactate and lactic acid recovered by the recovery method can be produced by simple apparatus, therefore more cost effective than conventional techniques requiring expensive equipments. The by-product, ammonium sulfate can be recycled as neutralizer for acid soil or as a protein purifier.

The present invention provides a method for producing lactide by using highly pure alkyl lactate or lactic acid recovered by the recovery method as the source material and through pre-polymerization, depolymerization process.

The lactic acid and alkyl lactate recovered from the recovery method is highly pure, therefore may be used as the source material for lactide synthesis, which then becomes the source material for poly lactide (PLA). The lactide may be produced by pre-polymerization, depolymerization process.

Alkyl lactate or lactic acid pre-polymer may be produced by pre-polymerizing the lactic acid or alkyl lactate recovered by the recovery method, and the pre-polymer may be depolymerized to poly lactide monomer, lactide by depolymerizing at high temperature vacuum condition.

The highly pure alkyl lactate recovered from the recovery method may be trans-esterified under titanium type catalyst or catalyst compound containing titanium type catalyst to produce lactide.

The alkyl lactate recovered by the recovery method is highly purity, therefore may be used as the source material for synthesis of lactide, which then becomes the source material for polylactide (PLA). The highly pure alkyl lactate recovered from the recovery method may be trans-esterified under titanium type catalyst or catalyst compound containing titanium type catalyst to produce lactide.

Hereinafter, the present invention will be described in more detail with reference to the following examples and experimental examples. However, the following examples and experimental examples are provided for illustrative purposes only, and the scope of the present invention should not be limited thereto in any manner.

Example 1

Production of Methyl Lactate and Lactic Acid

Step 1: The fermentation was carried out by using medium containing 20 weight % glucose, 0.5 weight % yeast extract, 0.05 weight % $K_2HPO_5$, 0.05 weight % $KH_2PO_4$, 0.1 weight % sodium acetate, 0.02 weight % $MgSO_47H_2O$ and 30 ppm $MnSO_47H_2O$ and *Lactobacillus paracasei* under an anaerobic condition at 35° C. The pH of the fermentation liquid was adjusted to pH 5.5 using 25 weight % of ammonia solution. Two days after fermentation, the powdered pellet was removed by centrifugation. Particles and bacteria were removed by ultra filtration to produce a lactic acid fermentation liquid with the purity of 96% L-type optical isomer and 4% D-type optical isomer. The final concentration of lactic acid in the lactic acid fermentation liquid was 16.8 g/L.

Step 2: Seventy five grams of water was dehydrated from 100 g of lactic acid fermentation liquid using rotary evaporator for 2 hrs at 50° C.

Step 3: 25 g of methanol and 12 g of 98% sulfuric acid were added to the dehydrated lactic acid fermentation liquid produced from step 2, and then stirred for 1 hr at room temperature.

Step 4: The ammonium sulfate precipitate generated after stirring in step 3 Was removed by filtration. The amount of ammonium sulfate separated and removed was 15 g.

Step 5: Esterification reaction was conducted for 6 hrs after heating the filtrate from step 3 at 65° C. After the reaction, the filtrate was analyzed by gas chromatography. The amount of methyl lactate produced was 13 g.

Step 6: Methanol was separated by first distillation for 2 hrs at 70° C. under normal pressure. Twelve grams of methyl lactate was separated by second distillation at 80° C., 100 mmHg pressures. The purity of methyl lactate from the second distillation was 95%.

Step 7: Ten grams of methyl lactate separated from step 6 was mixed with 150 g water and 1 g of Amberlyst-36 catalyst and then fed into the reactor connected with distillation apparatus for hydrolysis. The temperature of the reactor was maintained at constant temperature of 100° C. The amount of lactic acid produced 1 hr after hydrolysis was 7 g.

Example 2

Production of Ethyl Lactate and Lactic Acid

Step 1: The fermentation was carried out by using medium containing 20 weight % glucose, 0.5 weight % yeast extract, 0.05 weight % $K_2HPO_5$, 0.05 weight % $KH_2PO_4$, 0.1 weight % sodium acetate, 0.02 weight % $MgSO_47H_2O$ and 30 ppm $MnSO_47H_2O$ and *Lactobacillus paracasei* under an anaerobic condition at 35° C. The pH of the fermentation liquid was adjusted to pH 5.5 using 25 weight % of ammonia solution. Two days after fermentation, the powdered pellet was removed by centrifugation. Particles and bacteria were removed by ultra filtration to produce lactic acid fermentation liquid with the purity of 96% L-type optical isomer and 4% D-type optical isomer. The final concentration of lactic acid in the lactic acid fermentation liquid was 16.8 g/L.

Step 2: Seventy five grams of water was dehydrated from 100 g of lactic acid fermentation liquid by using rotary evaporator for 2 hrs at 50° C.

Step 3: 35 g of ethanol and 12 g of 98% sulfuric acid was added to the dehydrated lactic acid fermentation liquid produced from step 2, and stirred for 2 hrs at room temperature.

Step 4: The ammonium sulfate precipitate generated after stirring from step 3 was removed by filtration. The amount of ammonium sulfate separated and removed was 15 g.

Step 5: Esterification reaction was conducted for 10 hrs after heating filtrate from step 3 at 78° C. After the reaction, the filtrate was analyzed by gas chromatography. The amount of ethyl lactate produced was 15 g.

Step 6: Ethanol was separated by first distillation for 2 hrs at 85° C. under normal pressure. Fourteen grams of ethyl lactate was separated by second distillation at 100° C., 100 mmHg pressures. The purity of methyl lactate from the second distillation was 95%.

Step 7: Ten grams of ethyl lactate separated from step 6 was mixed with 150 g water and 1 g of Amberlyst-36 catalyst and then fed into the reactor connected with distillation apparatus for hydrolysis. The temperature of the reactor was maintained at constant temperature of 120° C. The amount of lactic acid produced 1 hr after hydrolysis was 8 g.

Example 3

Production of N-Propyl Lactate and Lactic Acid

Step 1: The fermentation was carried out by using medium containing 20 weight % glucose, 0.5 weight % yeast extract, 0.05 weight % $K_2HPO_5$, 0.05 weight % $KH_2PO_4$, 0.1 weight % sodium acetate, 0.02 weight % $MgSO_4 7H_2O$ and 30 ppm $MnSO_4 7H_2O$ and *Lactobacillus paracasei* under an anaerobic condition at 35° C. The pH of the fermentation liquid was adjusted to pH 5.5 using 25 weight % of ammonia solution. Two days after fermentation, the powdered pellet was removed by centrifugation. Particles and bacteria were removed by ultra filtration to produce lactic acid fermentation liquid with the purity of 96% L-type optical isomer and 4% D-type optical isomer. The final concentration of lactic acid in the lactic acid fermentation liquid was 16.8 g/L.

Step 2: Seventy five grams of water was dehydrated from 100 g of lactic acid fermentation liquid by using rotary evaporator for 2 hrs at 50° C.

Step 3: 50 g of n-propanol and 12 g of 98% sulfuric acid was added to the dehydrated lactic acid fermentation liquid produced from step 2, and stirred for 2 hrs at room temperature.

Step 4: The ammonium sulfate precipitate generated after stirring from step 3 was removed by filtration. The amount of ammonium sulfate separated and removed was 15 g.

Step 5: Esterification reaction was conducted for 12 hrs after heating the liquid produced after filtration from step 3 at 95° C. After the reaction, the filtrate was analyzed by gas chromatography. The amount of n-propyl lactate that was produced was 16 g.

Step 6: n-propanol was separated by first distillation for 2 his at 100° C. under normal pressure. Fifteen grams of n-propyl lactate was separated by second distillation at 130° C. and pressure of 100 mmHg. The purity of n-propyl lactate from the second distillation was 95%.

Step 7: Ten grams of n-propyl lactate separated from step 6 was mixed with 150 g water and 1 g of the catalyst, Amberlyst-36 and then fed into the reactor connected with distillation apparatus for hydrolysis. The temperature of the reactor was maintained at a constant temperature of 130° C. The amount of lactic acid produced 1 hr after hydrolysis was 9 g.

Example 4

Production of Highly Pure Lactide from Lactic Acid

Fifty grams of lactic acid produced from Example 1 was dehydrated for 2 hrs at 110° C. and the pressure of 700 Torr. Keeping the same pressure, the temperature of the reactor was increased to 200° C. and reacted for another 6 hrs to obtain 33 g of oligomer with the molecular weight of 3000 g/mole. Ten grams of oligomer obtained was mixed with 0.05 g of SnO catalyst before adding to the depolymerization reactor, and reacted for 2 hrs at the pressure of 10 Torr to obtain 6.6 g of lactide. The purity of the lactide analyzed by gas chromatography was 98%.

One kg of lactide was vacuum distillated by keeping the vacuum pressure under 10 Torr, and maintaining the column temperature in the range of 145 to 165° C. while using a distillation apparatus attached with a distillation column in the size of 30 mm in inner diameter and 1 m in length. The concentration of isolated lactic acid and water impurities in the purified lactide were 26 mmol/kg, therefore suggesting that the lactide purified was highly pure.

Example 5

Production of Ethyl Lactate from Lactide 1

Fifty grams of ethyl lactate produced from Example 2 was mixed with 0.5 g of catalyst, stannous octoate $[Sn(Oct)_2]$ under $N_2$ condition for 10 hrs at 160° C. and 700 Torr to obtain 30 g of oligomer with molecular weight of 2300 g/mole. Ten grams of oligomer obtained from above was added to the depolymerization reactor, and reacted for 2 hrs at 180° C. and 10 Torr to obtain 5.5 g of lactide. The purity of the lactide analyzed by gas chromatography was 98%.

Example 6

Production of Lactide from Ethyl Lactate 2

Lactide was produced by trans-esterification reaction of ethyl lactate produced from Example 2. The reaction system used composed of one-neck round bottom flask, where ethyl lactate was charged, a micro regulatory valve to control the flow of ethyl lactate with argon gas, three-necked round bottom flask where reaction occurred, double layer condenser which was connected to the three-necked round bottom flask to maintain the temperature from 20 to −10° C., automatic vacuum pump for pressure regulation in the reactor and silicon oil bath.

In this system, the three-necked round bottom flask completely removed of moisture was purged with argon gas before charging the reaction system with 0.17 mol of triethylene glycol dimethyl ether (TEGDME, dehydrated with Aldrich Molecular sieve) as catalyst and $2.5 \times 10^{-3}$ mol of titanium ethoxide $[Ti(OEt)_4, Acros]$. In addition, 0.34 mol of L-ethyl lactate produced from Example 2 was added to the moisture and air removed vial and connected to the reactor with a cannula. The pressure was maintained at 50 mmHg by passing argon gas to the inside of the reactor at 20 ml/min and using a vacuum pump. After putting the reactor in the silicon oil bath set at 120° C., the reactor was stirring to reach a temperature equilibration. Once equilibrated, L-ethyl lactate produced from Example 2 was injected into the reactor intermittently. The L-ethyl lactate was injected at the concentration of 0.17 mol during 1.5 hrs. Trans-esterification reaction was performed for 6 hrs to produce lactide. The conversion of L-ethyl lactate was 96% and the yield of lactide was 85.5% after the reaction. Also, the ethanol formed along with lactide by trans-esterification reaction was passed through the double layered condenser, condensed and collected in a two-necked round bottom flask that was placed in an ice water bath.

Experiment Example 1

Gas Chromatography Analysis

The ammonium sulfate removed filtrate from step 5 of Example 1 and lactide produced from Example 4 were analyzed by gas chromatography. Results are shown in FIGS. 2 and 3.

Figure 3:
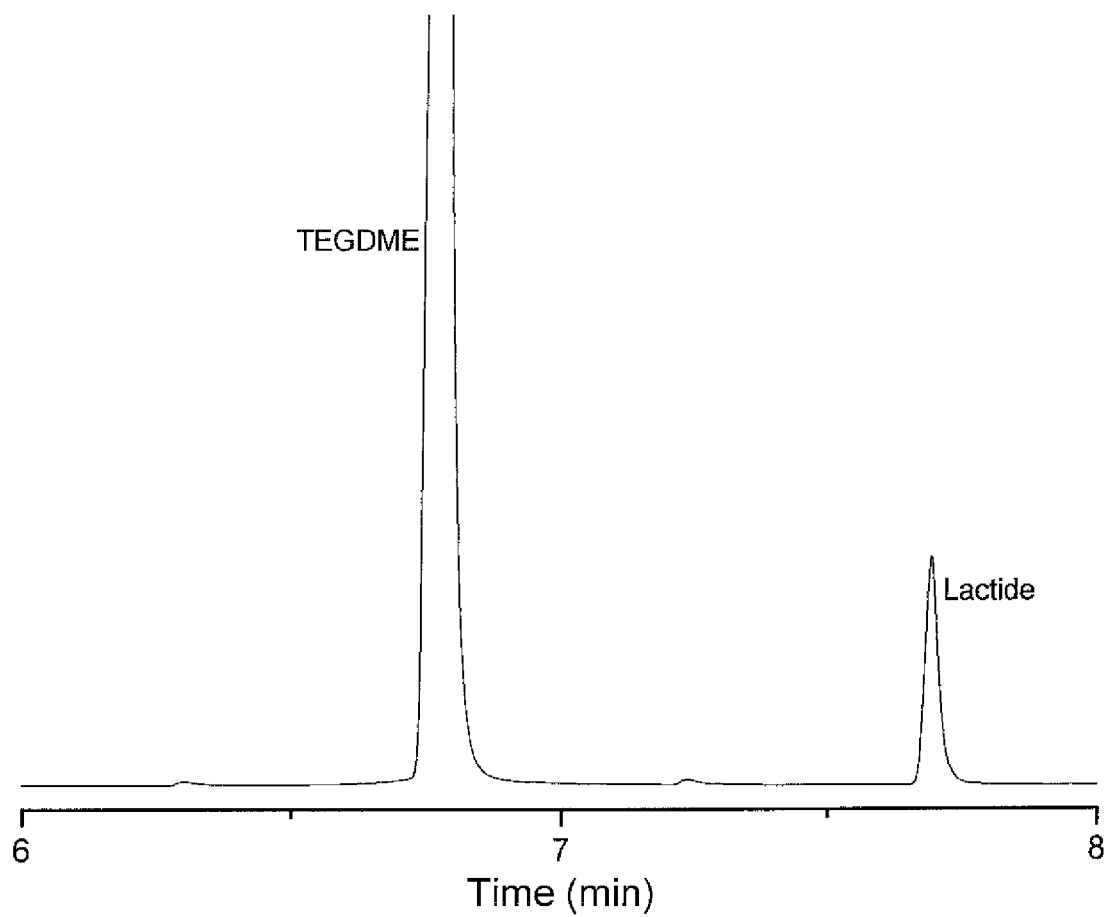
FIG. 3 is a graph showing the gas chromatography analysis of lactide produced from Example 4.

As shown in FIG. 2, methyl lactate was formed in the filtrate from Example 1; as shown in FIG. 3, lactide was formed from Example 4.

The recovery method of the present invention confirmed the recovery of alkyl lactate and lactic acid, and also, a highly pure lactide is produced when producing lactide using the alkyl lactate and lactic acid as the source material.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for recovering alkyl lactate, comprising:
   step 1: producing a source liquid comprising lactic acid or ammonium lactate;
   step 2: dehydrating the source liquid product of step 1;
   step 3: producing a liquid mixture by sequentially adding and stirring an alcohol and an acid solution to the dehydrated source liquid of step 2;
   step 4: separating and removing ammonium salt precipitate from the liquid mixture of step 3;
   step 5: producing an alkyl lactate from the ammonium salt-free liquid mixture by carrying out an esterification reaction; and
   step 6: separating an alcohol and alkyl lactate by distilling the mixture of step 5,
   wherein the alcohol of step 3 is selected from the group consisting of methanol, ethanol, normal propanol and isopropanol.

2. The method as set forth in claim 1, wherein the source liquid is produced from lactic acid fermentation liquid.

3. The method as set forth in claim 2, wherein the lactic acid fermentation liquid is produced by lactic acid-fermenting microorganism.

4. The method as set forth in claim 1, wherein the source liquid of step 2 is 50 to 95 weight % dehydrated.

5. The method as set forth in claim 1, wherein the dehydration of step 2 is performed at temperatures of 30 to 120° C. under a reduced pressure condition with respect to atmospheric pressure.

6. The method as set forth in claim 1, wherein the alcohol of step 3 is added at 1 to 10 fold molar ratio of lactic acid or ammonium lactate contained in the source liquid.

7. The method as set forth in claim 1, wherein in the acid solution in step 3 is one selected from the group consisting of sulfuric acid, hydrogen iodide (HI), hydrogen bromide (HBr), nitric acid ($HNO_3$), hydrochloric acid (HCl), phosphoric acid ($H_3PO_4$), perchloric acid ($HClO_4$), and a mixture thereof.

8. The method as set forth in claim 1, wherein the acid solution of step 3 is added at 0.3 to 3 fold molar ratio of lactic acid or ammonium lactate contained in the source liquid.

9. The method as set forth in claim 1, wherein the acid solution of step 3 is added at 0.5 to 1 fold molar ratio of lactic acid or ammonium lactate contained in the source liquid.

10. The method as set forth in claim 1, wherein the esterification reaction of step 5 is performed at temperatures of 30 to 150° C.

11. The method as set forth in claim 1, wherein the esterification reaction of step 5 is performed at temperatures of 50 to 100° C.

12. A method to recover of lactic acid comprising hydrolyzing the highly pure alkyl lactate recovered by the method of claim 1.

13. The method as set forth in claim 12, wherein the hydrolysis is performed at temperatures of 30 to 200° C.

14. The method as set forth in claim 12, wherein the hydrolysis is performed at temperatures of 60 to 150° C.

15. The method as set forth in claim 12, wherein the hydrolysis is performed in a hydrolysis reactor containing acid catalyst or base catalyst.

16. The method as set forth in claim 15, wherein the acid catalyst is selected from the group consisting of sulfuric acid, ion exchange resin, sulfonated tetrafluoroethylene based fluoropolymer-copolymer, sulfonated tetrafluoroethylene based fluoropolymer-copolymer-silica composite, $Hb_2O_5$, $HNbMoO_6$, zeolite, and $H_{(8-n)}XM_{12}O_{40}$ ($X=Si^{4+}$ or $P^{5+}$; $M=W^{6+}$ or $Mo^{6+}$; $n=4$ when $X=Si^{4+}$ and $n=3$ when $X=P^{5+}$).

17. The method as set forth in claim 15, wherein the base catalyst is selected from the group consisting of alkali or alkali earth metal hydroxide, basic oxide containing alkali or alkali earth metal ion, and hydrotalcite-class Layered Double Hydroxide (LDH).

18. A method producing a lactide comprising:
   producing lactide through a pre-polymerization process, a depolymerization process, and a reduced-pressure distillation process by using alkyl lactate or lactic acid recovered by the method of claim 1; or
   hydrolyzing the alkyl lactate recovered by the method of claim 1 as a base material.

19. The method as set forth in claim 18, wherein the producing the lactide is performed using the alkyl lactate as the base material through a trans-esterification reaction using a titanium type catalyst or a catalyst compound containing titanium type catalyst.

* * * * *